United States Patent [19]

Pinkerton

[11] 4,096,059
[45] * Jun. 20, 1978

[54] PROPORTIONING FLUIDS

[76] Inventor: Harry E. Pinkerton, Bridle Path La., Mill Neck, N.Y. 11765

[*] Notice: The portion of the term of this patent subsequent to Jul. 26, 1994, has been disclaimed.

[21] Appl. No.: 759,595

[22] Filed: Jan. 14, 1977

Related U.S. Application Data

[63] Continuation-in-part of Ser. No. 685,564, May 12, 1976, Pat. No. 4,037,616, which is a continuation-in-part of Ser. No. 590,897, Jun. 27, 1975, abandoned.

[51] Int. Cl.² .............................................. B01D 13/00
[52] U.S. Cl. .................................... 210/22 A; 137/99; 417/391; 210/321 B
[58] Field of Search ......... 137/99; 210/321 A, 321 B, 210/22; 417/250, 391–395; 222/134, 136, 137

[56] References Cited

U.S. PATENT DOCUMENTS 3,976,574  8/1976  White ........................... 210/321 A X
4,037,616  7/1977  Pinkerton ................................ 137/99

Primary Examiner—Frank A. Spear, Jr.
Attorney, Agent, or Firm—Nolte and Nolte

[57] ABSTRACT

Apparatus for accurately proportioning and mixing fluids comprising a double acting piston/cylinder unit of which the cylinder is divided into two chambers by the piston and the volume of the cylinder swept by the piston at one end of the piston is lesser than that at the other end. An inlet connection for a first fluid is made to one chamber, a conduit connects the two chambers and includes a connection to a source of the second fluid. Valve means are associated with the conduits and are effective to cause a charge of first fluid to be delivered to said one chamber and thereafter to be transferred to the other chamber drawing fluid from said source of second fluid to make up for the difference in the volumes of the chambers. Said valve means then cooperate to cause the mixed fluids to be discharged from the other chamber as said one chamber is again charged with said first fluid. In a variant of the invention the piston/cylinder unit is replaced by a receptacle within which is disposed a diaphragm the diaphragm serving to divide the receptacle into two chambers. In other variants means are provided for varying the ratio of first to second fluid in the mixture and in still other variants the second fluid is made up of components of two or more fluids the ratios of those components being adjustable.

19 Claims, 11 Drawing Figures

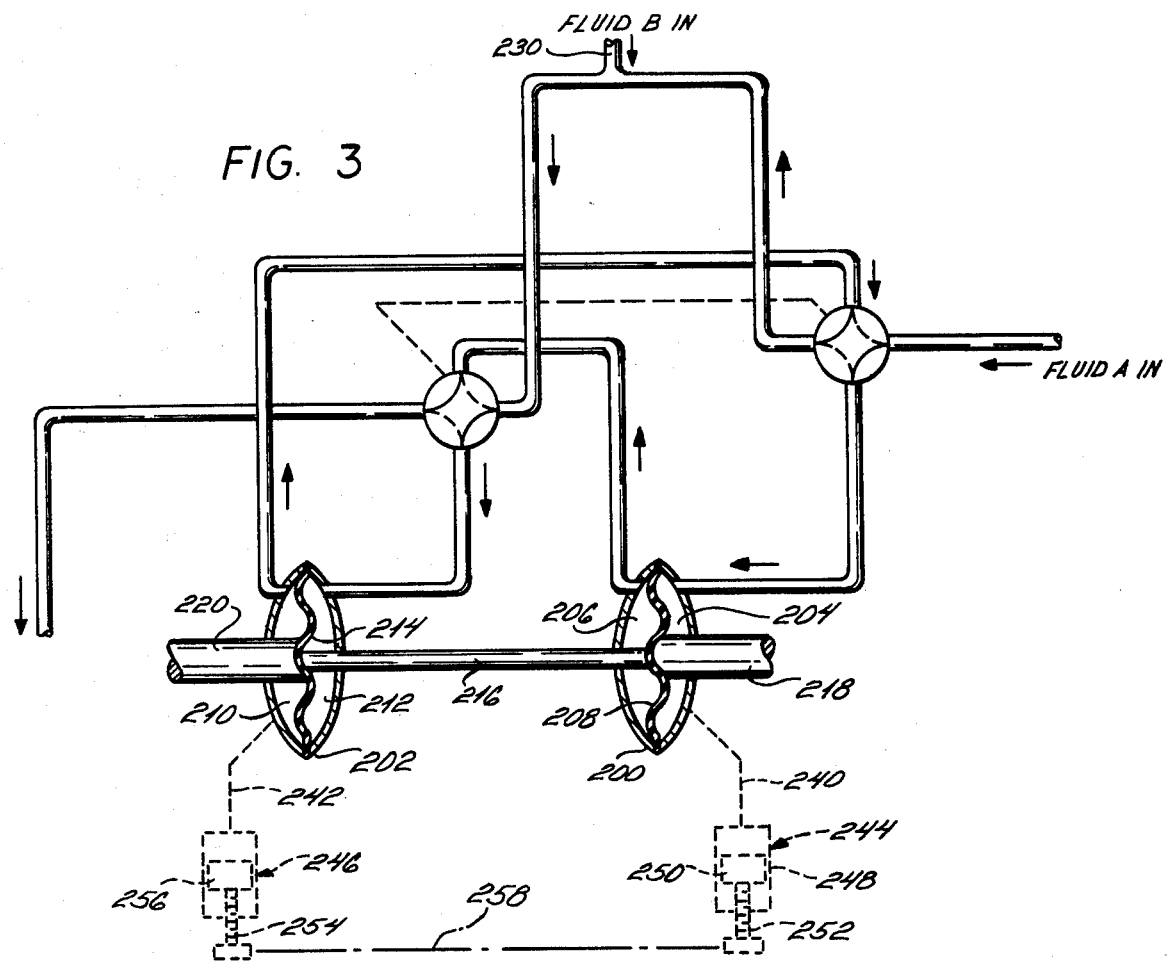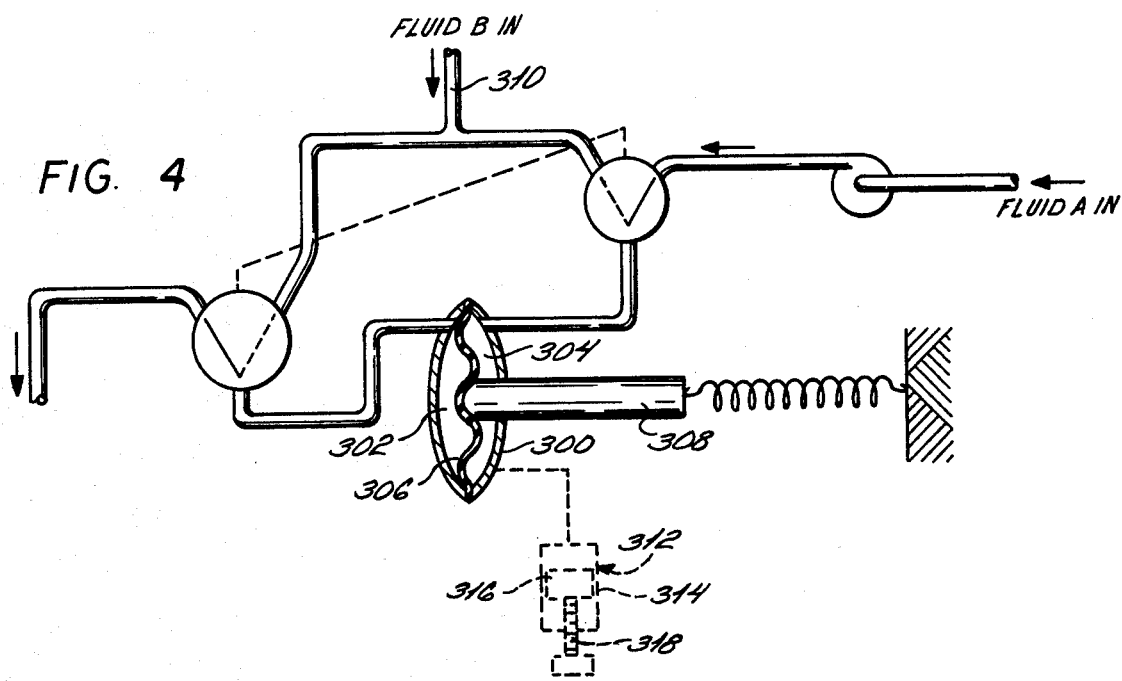

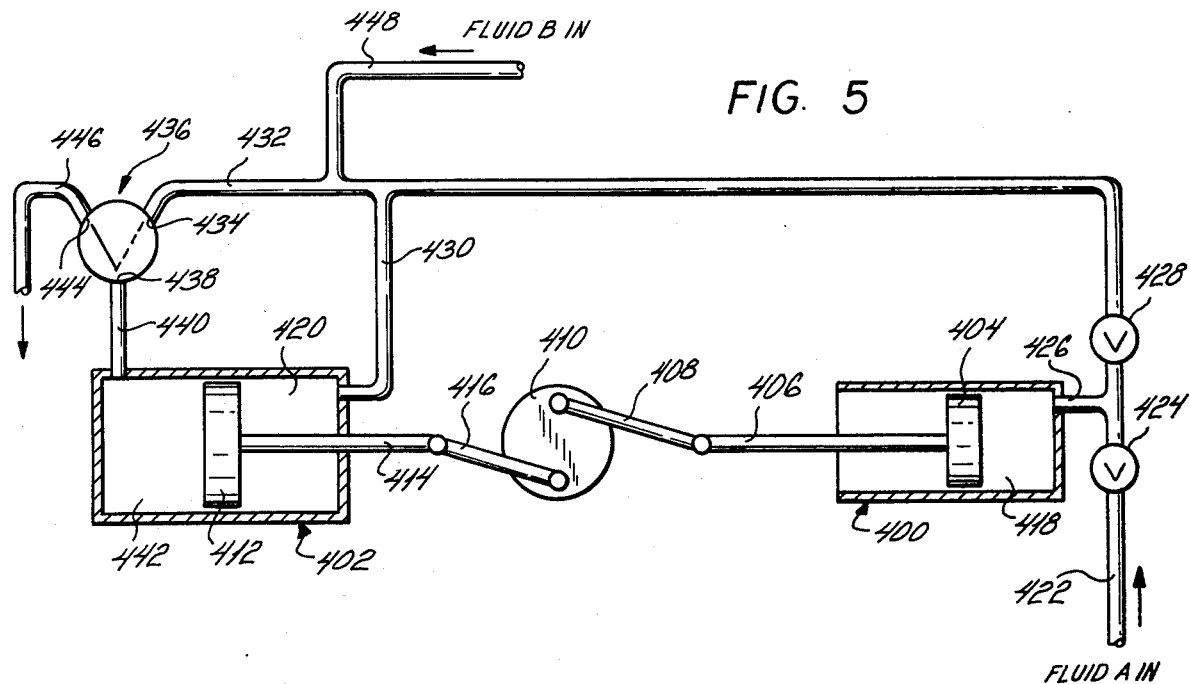
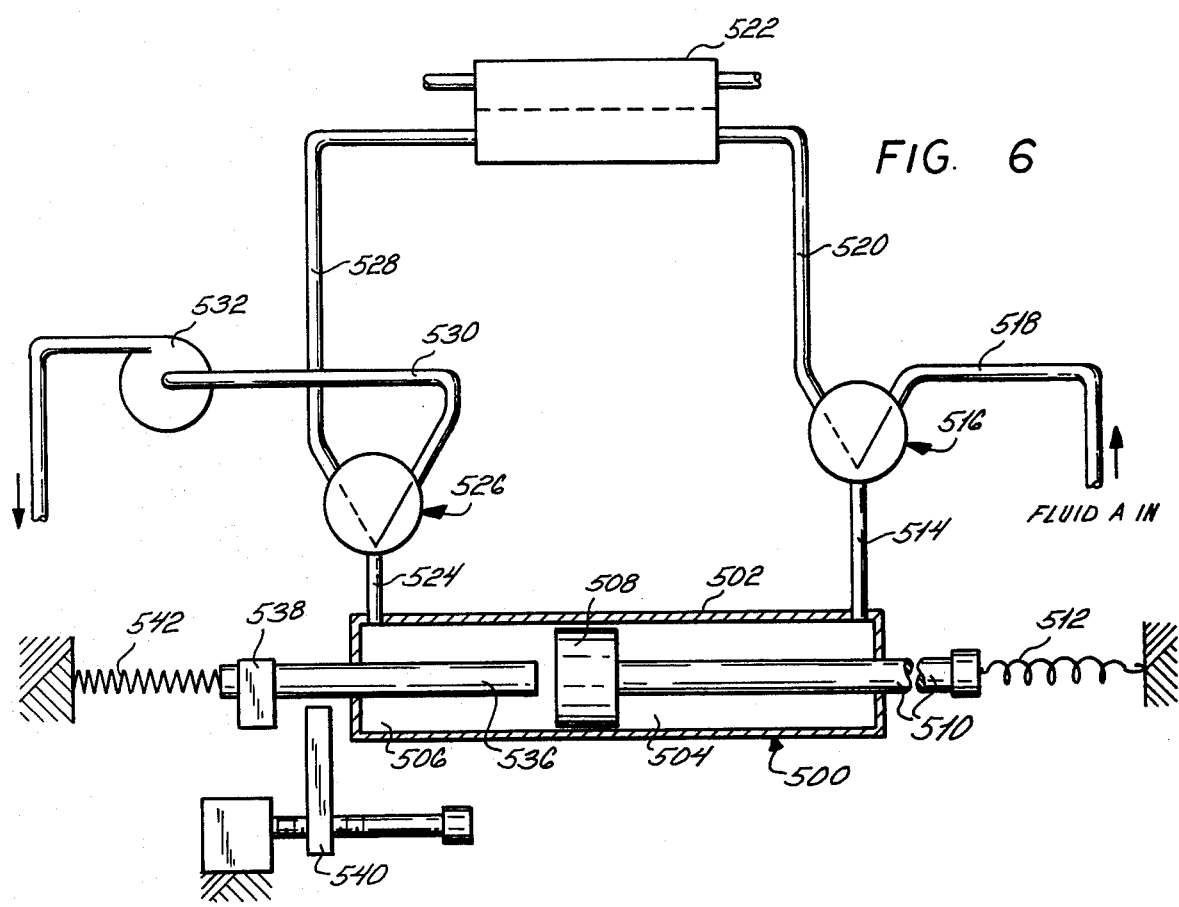

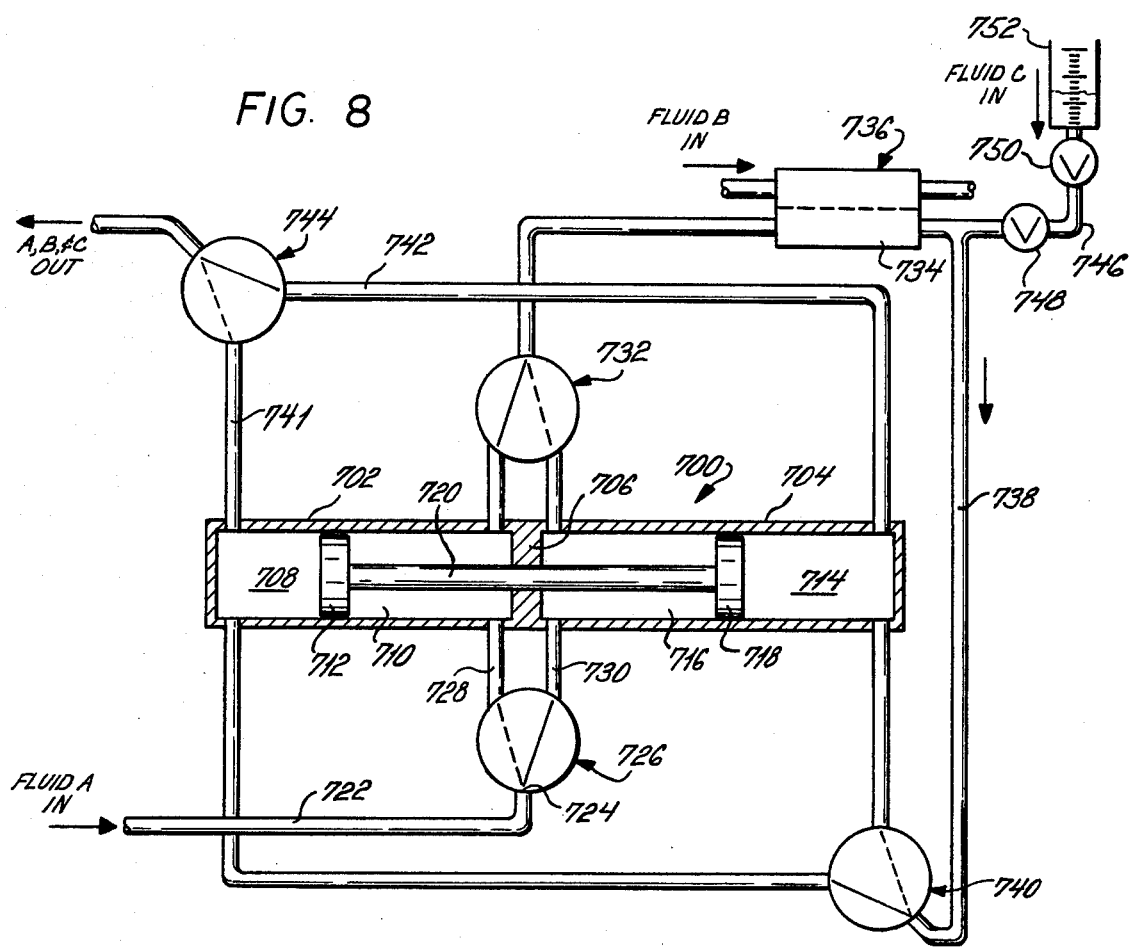
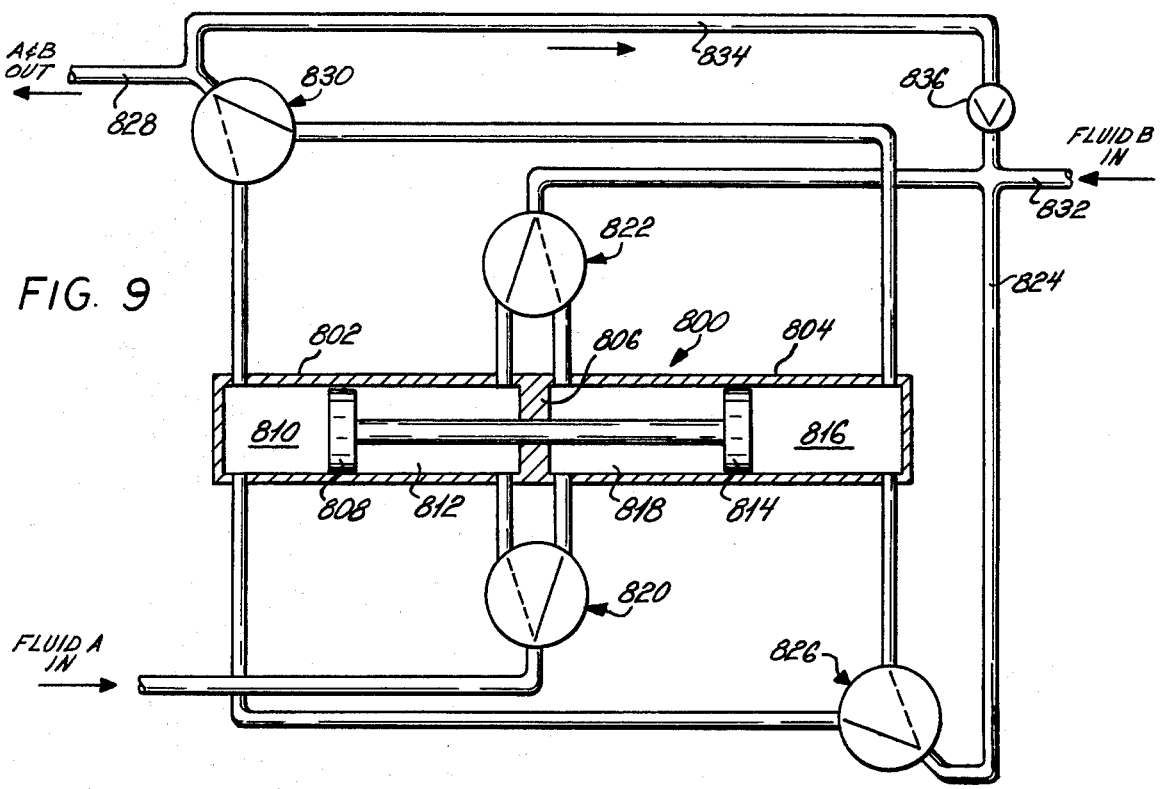

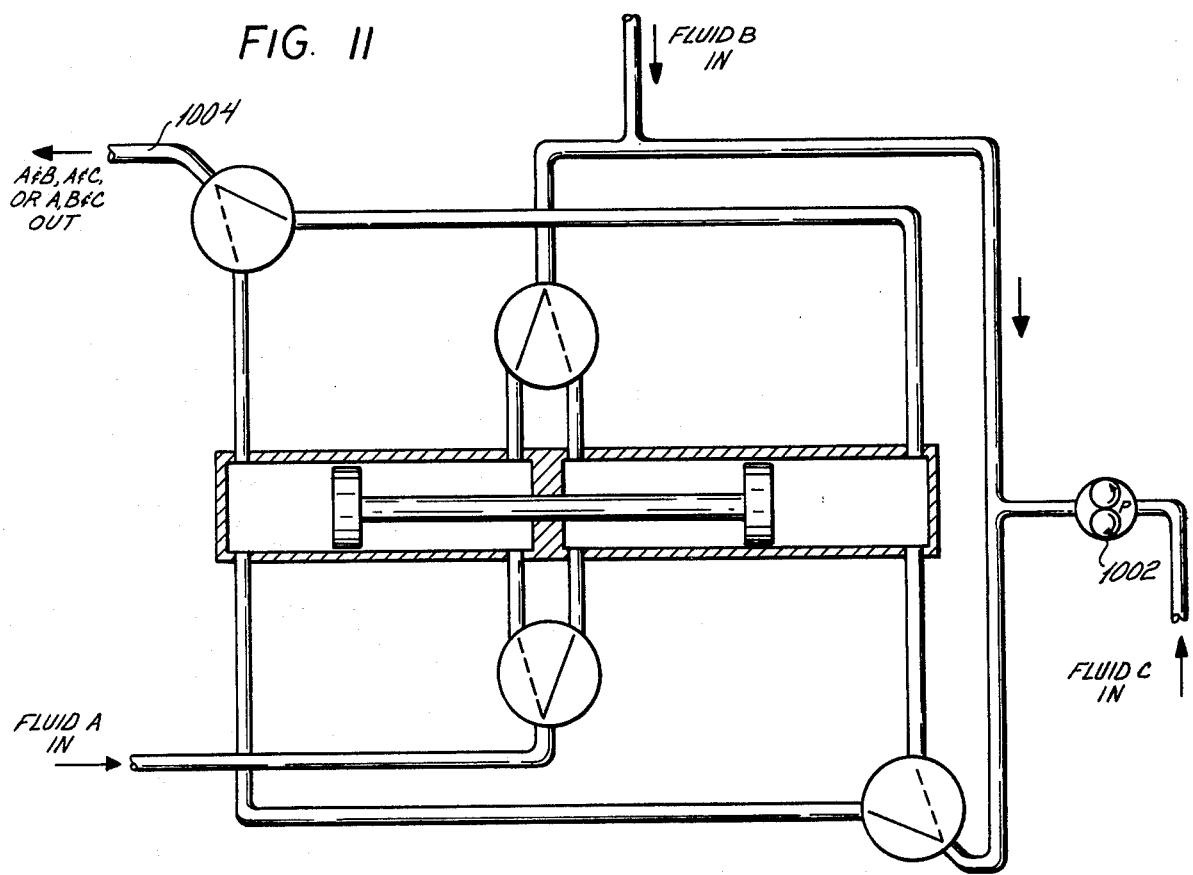

PROPORTIONING FLUIDS

REFERENCES TO RELATED APPLICATIONS

This application is a continuation-in-part of application Ser. No. 685,564, filed May 12, 1976, now Pat. No. 4,037,616, which in turn is a continuation-in-part of application Ser. No. 590,897 filed June 27, 1975, now abandoned.

BACKGROUND OF THE INVENTION

This invention is concerned with apparatus for and a method of accurately proportioning and mixing fluids and is particularly, but by no means exclusively, concerned with such apparatus and method used in dialysis systems, first for the accurate proportioning and mixing of the two fluids which constitute the component parts of dialysate solutions, and secondly, for controlling the proportionate relationship between the dialysate solution and the waste material drawn from the blood of a patient across the membrane of a dialysis cell in the classical hemodialysis procedure. It is of course to be appreciated in these two cited instances that while mixing of the fluids will occur, the primary purpose is not such mixing but rather the controlled proportioning of merging fluid streams.

In the past, mixing of fluids in predetermined ratios has often been effected by the utilization of two or more positive displacement pumps, each handling a separate fluid and delivering to a chamber in which mixing occurs. Typical of prior art arrangements are the structures shown in Arp's U.S. Pat. Nos. 3,530,872 and 3,530,873, both issued Dec. 29, 1970. These patents are primarily designed for utilization in respirator systems where oxygen is mixed with air and, as such, extremely close adherence to the desired proportions of fluids in the mixture is not as critical. However, from a consideration of those patents, it will be apparent that they cannot deliver a closely controlled mixture of fluids.

Referring, for example, to U.S. Pat. No. 3,530,872 which shows a double acting piston/cylinder unit for handling the oxygen of the mixture and of which the piston is ganged to a single acting piston/cylinder for handling the air or other fluid, it will be apparent, considering FIG. 2 of that patent, that the quantity of oxygen moved from one side to the other of the double acting piston as that piston moves from right to left, will be in excess of that which can be accommodated on the other side of the piston and therefore that excess oxygen must pass to the outlet and, of course, will not be mixed with the second fluid.

U.S. Pat. No. 3,530,873 shows a pair of double acting piston/cylinder units one of which meters the oxygen supply and the other of which meters air or another fluid, the pistons of the two units being ganged by a common piston rod.

Referring to FIG. 3 of the drawings of that patent, again it is apparent that the volume of oxygen delivered to the outlet line is greater in left to right movement of the pistons than it is in right to left movement, whereas exactly the opposite is true of the second fluid. As such, there is substantial error introduced in the proportions of the fluids in the mixtures produced by that system.

Malburg's U.S. Pat. No. 2,203,832 issued June 11, 1940 purports to show a system for accurately proportioning and mixing two liquids one of which is water and the other of which is embalming fluid. Since Malburg is concerned with a treatment of cadavers the strictest accuracy is probably not necessary but a consideration of this patent will reveal that error must occur in his proportioning device. Referring to FIG. 1 of the patent, it is clear that the amount of embalming fluid delivered to be mixed with water during right to left movement of the pistons will exceed that amount delivered to be so mixed on left to right movement of the pistons. Since there is a by-pass between opposite sides of the piston in the cylinder from which the embalming fluid is delivered and since an additional mixing piston/cylinder device is provided this error may be lessened to acceptable limits considering that the resultant mixture is utilized only on cadavers. Nonetheless, the error is present and no attempt is made to correct it.

Apparatus utilized in hemodialysis procedures for mixing liquids in accurate proportions is shown in Willock's U.S. Pat. No. 3,598,727 issued Aug. 10, 1971. In that apparatus a double acting piston/cylinder unit has a pair of piston rods which extend from opposite ends of the cylinder in which the first liquid (usually water) is handled and each one extends into a corresponding one of two cylinders connected to supply of a second fluid (a dialysate concentrate). The liquids are delivered through a spool valve to be mixed before being admitted to a dialysis cell.

While Willock's apparatus may be accurate, it of course requires multiple piston and cylinder units and complex valving to unite the liquids.

BRIEF SUMMARY OF THE INVENTION

The present invention seeks to avoid these disadvantages by the provision of a proportioning and mixing device comprising a piston/cylinder unit in which the volume swept by the piston at one end thereof is lesser than that at the other end thereof, in which a first fluid is delivered to the lesser volume end during movement of the piston in one direction and is transferred from that side of the piston to the other during movement in the opposite direction, there being a connection from a supply of a second fluid into the system so that the difference in volume be made up by the second fluid. By the selection of appropriate component dimensions to form a specific difference in volume, a particular ratio of the fluids can be established and accurately maintained and by the adoption of novel adjustment means that ratio can be varied as desired.

The invention also embodies a variation in which the piston/cylinder unit is replaced by a simple receptacle divided into two chambers by a diaphragm element which is caused to flex alternately to expand and contract the two chambers, means being provided to render the volume of first fluid delivered to one chamber to be lesser than that volume required to fill the other chamber upon expansion of said other chamber so that second fluid is introduced into the system in a volume equal to the difference in the aforementioned volumes.

According to another aspect of this invention there is provided a method of mixing liquids which consists in filling a first expansible chamber with a first liquid to establish a determined volume of first liquid in said chamber, making a connection between said chamber and a second expansible chamber and causing said first liquid to be delivered to said second chamber, making a connection from a source of second liquid to said connection between said chambers and causing said second chamber to expand to a second volume greater than said determined volume to cause said second liquid to be admitted to said second chamber in a volume equal to the difference between said determined and second volumes.

It is to be recognized that the second liquid discussed above with respect to the several aspects of the invention may of course consist of two or more different liquids or different sources of the same liquid, and that the admission of those liquids can be independently controlled to obtain desired mixtures.

BRIEF DESCRIPTION OF THE DRAWINGS

Embodiments of the invention are illustrated in the accompanying drawings, in which:

FIG. 3 shows, schematically, a double acting form of the invention;

FIG. 4 shows a single acting form of the invention;

FIG. 5 shows, schematically, a single acting form of the invention;

FIG. 6 shows a single acting form of the invention with means for adjusting the proportion of fluids;

FIG. 8 shows an alternative double acting form of the invention;

FIG. 9 shows another double acting form of the invention;

FIG. 11 shows yet another embodiment of the invention.

DESCRIPTION OF THE PREFERRED EMBODIMENTS

Figure 1:
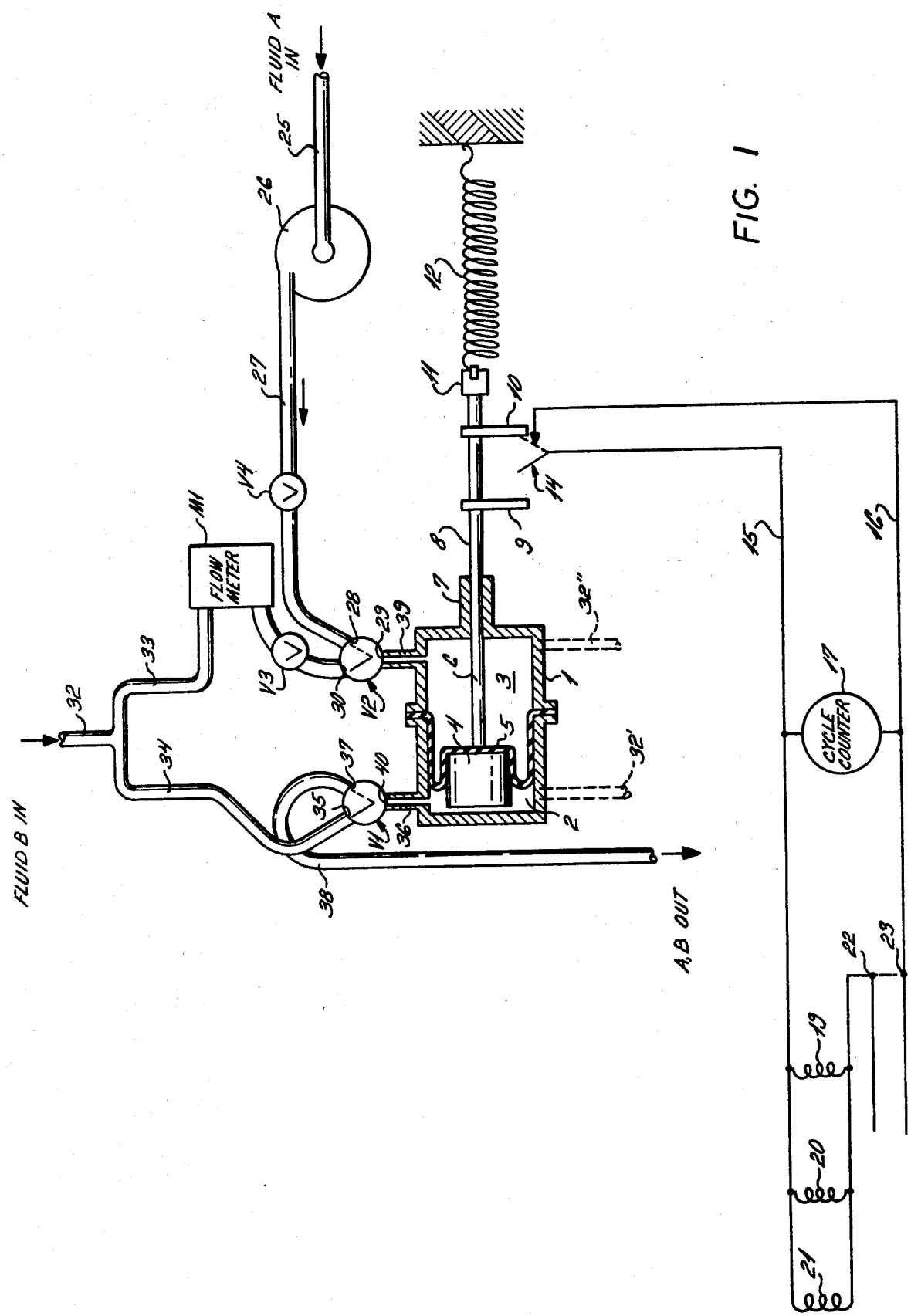
FIG. 1 shows, schematically, a single acting embodiment of this invention.

The apparatus of FIG. 1 comprises a (piston/)cylinder unit 1 which is divided into chambers 2 and 3 by a piston unit 4 which has a rolling diaphragm 5. Extending from one end of the piston is a piston rod 6 guided in an extension 7 of an end wall of the cylinder.

The region 8 of the piston rod outside of the cylinder 1 is provided with adjustable stop means 9 and 10 which cooperate, in a manner to be described hereinafter, with a switch indicated generally at 14. Secured to the end of the piston rod at 11 is a spring 12, the other end of that spring being fixed so that the spring is effective to bias the piston from left to right.

The switch 14 is included in a circuit 15, 16 which comprises a cycle counter 17 (the purpose of which is described hereinafter) and coils 19 and 20 of solenoids associated with valves and motor 21 which drives the pump 26 as hereinafter described. A connection to an electrical supply is made at terminals 22 and 23.

A first fluid inlet 25, that is to say an inlet for a first fluid, is made through centrifugal pump 26 to line 27 which includes metering valve V4 which, as will be apparent from the following description, controls the velocity of right to left piston movement. From the metering valve V4 the line 27 extends to a first port 28 in three port valve V2, through said valve V2 to common valve port 29 which is connected to cylinder port 39 leading to chamber 3 of cylinder 1.

A connection is made between chamber 3 of cylinder 1 and chamber 2 by means of cylinder port 39 and valve port 29, which have a common role as a part of the first fluid inlet and as a part of the conduit connecting the two chambers of the cylinder, that latter conduit being completed through third port 30 in valve V2, a regulating valve V3 (which controls left to right piston velocity) and line 33 to line 34 through a three port valve V1 and cylinder port 36. A branch 32 extends into lines 33 and 34 at a T and is connected to a supply of a second fluid. Conveniently, a single flow meter M1 is disposed in the line 33 which may be calibrated and read in units of flow rate for each of the two fluid streams since, of course, the two flow rates are directly related to each other in a fixed proportional relationship.

An outlet conduit from chamber 2 is constituted by cylinder port 36 which, as is the case with cylinder port 39, has a common role as both an inlet to chamber 2 and as an outlet from that chamber, the outlet from chamber 2 being completed through valve V1 at port 37 to an outlet line 38.

The operation of the device is as follows:

As the piston 4 completes its stroke from right to left, the switch 14 will be thrown by the adjustable stop 10 causing de-activation of the solenoids in circuit 15/16 so that valves V1 and V2 will adopt the positions shown in full line at which time the delivery of the first fluid to chamber 3 by pump 26 will be ceased as the electrical supply to motor 21 is interrupted, and the piston 4 will begin its movement left to right under the influence of spring 12. At this time the fluid within chamber 3 will pass through valve V2, flow rate regulating valve V3, the flow meter and valve V1 to chamber 2 and, since the volume of fluid to be passed from chamber 3 to chamber 2, is less than the volume of fluid that will be demanded by chamber 2 during left to right piston movement, the excess fluid required to fill chamber 2 will be drawn in from the second fluid supply through line 32.

As the piston completes its left to right movement, stop 9 will activate switch 14 to cause the solenoids to shift the valve V1 and V2 to the position shown in chain line and motor 21 will be activated. At this time the first fluid will be admitted to the chamber 3 causing the piston to move from right to left and the fluid circuit between chambers 2 and 3 through valves V1 and V2 will be blocked, valve V1 making the connection between chamber 2 and outlet 38 so that the mixture of fluid in chamber 2 passes to outlet line 38 to be used as required or discarded.

It will be appreciated that in the construction hereinabove described the quantity of the second fluid drawn into the chamber 2 is directly related to the difference in volume between the chambers 2 and 3 which in turn is directly related to the cross-sectional area of the piston rod 6, or at least that part of the piston rod within the chamber 3, and the stroke distance traversed by the piston. Thus, by the careful selection of rod area to piston area ratio, one is able to establish a fixed proportion of the first and second fluids in the mixture which issues from outlet 38. Further, it will also be understood that, with the volumetric displacement of each piston stroke known for each of the two cylinder chambers 2 and 3 in the invention described in FIG. 1, cycle counter 17 provides the multiplier (cycles times stroke volume) to render conveniently visible the cumulative volume of said first fluid stream, second fluid stream and mixed streams at any time during continuous operation of the system, such as during a typical hemodialysis procedure. Thus, while the facility for accurately reading instantaneous flow rate values is provided by flow meter M1, such values are arbitratily adjustable through flow control valve V3, and the critical cumulative volume flow values, which may represent the difference between life and death for the hemodialysis patient, are continuously presented for surveillance by the operator of the dialysis system.

It is of course to be appreciated that the arrangement illustrated in FIG. 1 is schematic and shows a particularly desirable system in which the first fluid inlet to one side of a cylinder and the interconnection between the two sides of the cylinder includes a common branch, i.e. valve port 29. Further, the interconnection between the two sides of the cylinder and the outlet from chamber 2 includes a common portion constituted by valve port 40 and cylinder port 36. Additionally, the second fluid inlet has a common part with the interconnection between the two sides of the cylinder, that common part comprising line 34, valve ports 35 and 40 and cylinder port 36. However, by the utilization of further valving, single conduits for each of the purposes above discussed could be utilized. For example, and as shown in FIG. 1, second fluid inlet 32 could be replaced by either one of fluid inlets 32' and 32'', both shown in chain line, inlet 32' being made directly into chamber 2 of the cylinder 1 and inlet 32'' being made into chamber 3. It is to be appreciated that the mixing in such alternative arrangements will not, in all probability, be so effective as that in the illustrated preferred arrangement and that it would not be available where the direct admission of the second fluid to the cylinder may have adverse effects on the components of that cylinder, or the piston and seals within it.

Additionally, while in the particular arrangement illustrated a single pole single throw toggle switch type arrangement has been illustrated quite conceivably, and in some instances more desirably, that switch could be replaced by other switch means, as for example by photo cells or, since at the completion of each stroke there will be a pressure surge, that pressure surge may be sensed and utilized to effect switching of the valves as, for example, through the intermediary of a diaphragm.

Clearly, too, the apparatus could be modified so that instead of relying upon the pressure of the delivery of the first fluid and the spring for movement of the piston, a positive mechanical drive could be applied to the piston with appropriate modifications of the piston to cylinder seals.

Figure 2:
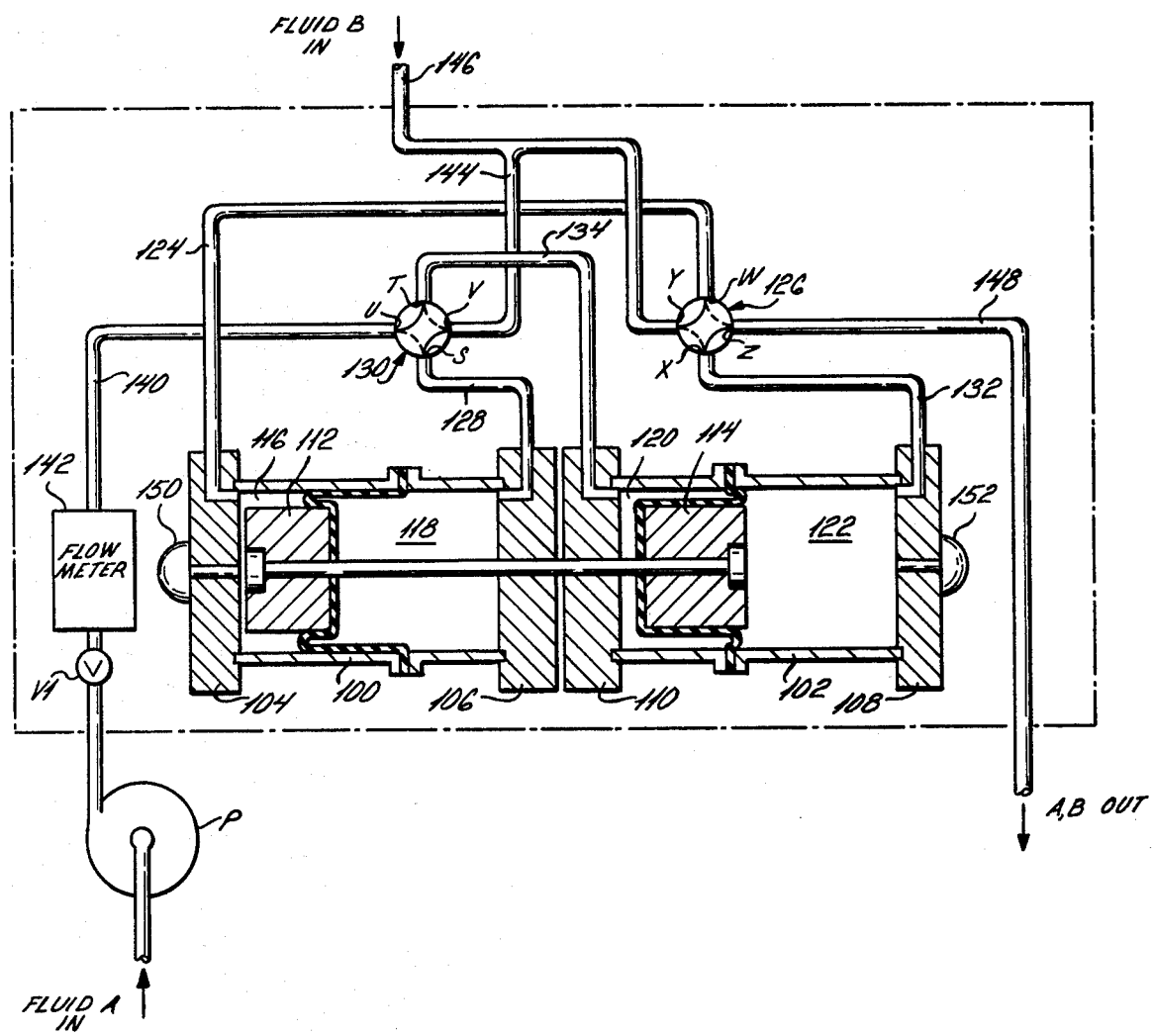
FIG. 2 shows a double acting form of the invention, again, schematically.

In FIG. 2, there is shown an arrangement, in many respects resembling that of FIG. 1, but in which there are two piston/cylinder units. To distinguish clearly between the embodiments of FIG. 1 and FIG. 2 parts of the apparatus of FIG. 2 are identified by different reference numerals than those utilized in the embodiments of FIG. 1.

The apparatus of FIG. 2 comprises a left hand cylinder 100 and a right hand cylinder 102. The ends of cylinder 100 are closed by port plates 104 and 106 and those of cylinder 102 are closed by port plates 108 and 110.

Disposed within cylinders 100 and 102 are pistons 112 and 114, respectively, each provided with a conventional rolling diaphragm seal so that cylinder 100 is divided into chambers 116 and 118 at opposite sides of the piston and cylinder 102 is divided into chambers 120 and 122 to each side of piston 114. It is to be noted that the pistons are joined by a common piston rod sliding in port plates 106 and 110.

Leading from chamber 116 to port plates 104 conduit means 124 communicates with port W of a four port valve 126 and conduit 128 leads to port S of a four port valve 130 from chamber 118, through port plate 106.

Conduit 132 leads to port X of valve 126 from chamber 122 through port plate 108 and conduit 134 communicates between chamber 120 of cylinder 102 and port T of valve 130.

A first fluid inlet conduit 140 extends from a supply of first fluid, through a valve V1 and a flow meter 142, to port U of valve 130 and conduit 144 communicates between port V of valve 130 and port Y of valve 126, conduit 144 including a T having a branch 146 communicating with a source of a second fluid.

The valve 126 also includes a port Z communicating with conduit 148 which leads to an outlet for the mixed fluids.

Disposed in port plates 104 and 108 are proximity switches 150 and 152, respectively.

The operation of the device of FIG. 2 is as follows:

In the position shown in the drawings, i.e. with the pistons at the extreme left of their respective cylinders, port U of valve 130 is connected, as shown in full line, to port T and port S is connected to port V. In valve 126 port Y is connected to port W and port X is connected to port Z.

It is to be appreciated that the position of the valves 126 and 130 is to be controlled by solenoids actuated by one or other of switches 150, 152 in this embodiment shown as proximity switches, but obviously any type sensor compatible with the role of those switches, may be used to control articulation of the valves of the system as discussed, supra, with regard to the embodiment of FIG. 1.

In the meantime, first fluid supplied under adequate pressurization as for example provided by pump P but more likely provided by mains pressure to constitute the first fluid as a motive fluid for the piston system will be passed along conduit 140 through the flow meter 142 and flow rate regulator valve V1 to flow director valve 130 where it will move from port U to port T and through line 134 to chamber 120 of the cylinder 102.

Considering cylinder 100, as the piston 112 begins its movement from left to right, fluid contained in chamber 118 passes through ports S and V of valve 130 along conduit 144 to valve 126, through ports Y and W of that valve and through conduit 124 to chamber 116. Since the volume of fluid displaced from chamber 118 is lesser than that required to fill chamber 116, the difference in volume will be made up by the second fluid drawn from inlet 146.

At the same time, fluid in chamber 122 will be moved from that chamber to line 132 and via ports X and Z of valve 126 to line 148. It will be apparent from what follows that the fluid from chamber 122 will comprise a precise mixture of predetermined porportions of the first and second fluids.

As the pistons 112 and 114 approach the extreme right hand position, proximity switch 152 will be activated to cause appropriate solenoids, not shown in the drawings, to shift the positions of valves 126 and 130 so that the first fluid, will pass along conduit 140 from port U to port S of valve 130 to enter chamber 118 providing the motive force to shift the pistons from right to left. Fluid in chamber 116, as described hereinbefore, a predetermined mixture of the first and second fluids, will be moved along conduit 124 to pass from port W to port Z of valve 126 and along outlet 148. Similarly, fluid in chamber 120 will be moved along conduit 134 to pass from port T to port V of valve 130 and along conduit 144 to pass from port Y to port X of valve 126 and enter, along conduit 132, chamber 122. Since the volume of that first fluid is lesser than that required to fill chamber 122 the difference in volume will be made up by the second fluid drawn in through inlet 146.

As the device continues to operate, a substantially constant flow of a mixture of predetermined proportions will issue from line 148 to be utilized there as required or to be discarded, depending upon the purpose to which the device is put.

As with the apparatus of FIG. 1, it is to be appreciated that the structure of FIG. 2 is subject to various modifications which do not deviate from the scope of the invention as defined in the appended claims. For example, the pipe work exterior to the cylinders can be varied along with appropriate variations in the valving and, of course, while in this particular embodiment utilization of proximity switches has been described, clearly those devices could be replaced by any other appropriate sensors and valve articulation units. Also, and as with the apparatus of FIG. 1, it is often desirable to provide a cycle counter to obtain an indication of the cumulative volumes of the first, second and mixed fluid streams at any time during continuous operation of the device.

The embodiment of FIG. 3 is in many respects similar, in operation, to that of FIG. 2 and for this reason a description of the common features is not repeated. Essentially, the embodiment of FIG. 3 differs from that of FIG. 2 in that instead of piston and cylinder units, there are provided a pair of receptacles 200 and 202. Receptacle 200 is divided into chambers 204 and 206 by means of a flexible diaphragm 208. Similarly, receptacle 202 is divided into chambers 210 and 212 by means of a flexible diaphragm 214. The diaphragms are interconnected by a rod-like element 216 which extends through appropriately sealed openings in the receptacles and through chambers 206 and 212 respectively of receptacles 200 and 202. Projecting from the opposite side of diaphragm 208 and to the exterior of the receptacle 200 is another rod 218. A similar rod 220 projects from the diaphragm 214 through chamber 210 to the exterior of the receptacle 202.

It is to be noted that the rods 218 and 220 are similar and are of greater cross-section than rod 216 therefore constituting those rods 218 and 220 as means for reducing the volume of the first fluid admitted to chambers 204 and 210 to be lesser than that required to fill the chambers 206 and 212. With such an arrangement, it will be recognized that a volume of a second fluid will be drawn through second fluid inlet 230 to be admitted to chambers 206 and 212 respectively in a directly controlled relationship to the difference in cross-section of rods 218 and 216 and rods 220 and 216.

In certain situations, discussed infra, it is possible and desirable to vary the proportions of the two fluids in the mixture admitted to chambers 206 and 212 and to this end there may be provided, as indicated in chain line, connections 240 and 242 between chambers 204 and 210, respectively and piston/cylinder units 244 and 246. The piston/cylinder unit 244, and this is the same as piston/cylinder unit 246, comprises a cylinder element generally indicated at 248 within which there is disposed a piston or plunger member 250 the movement of which is limited by a screw threaded adjustable stop element 252. A similar screw threaded stop element 254 is associated with plunger member 256 of unit 246 and those stop elements are ganged as indicated in chain dot line at 258 so that any adjustment of one step element within its respective cylinder is reflected in the other unit. It will be appreciated that by adjusting the position of the stops the quantity of the first fluid drawn into chambers 204 and 210 will be varied, but of course the quantity of fluid required to fill chambers 206 and 212 will remain constant. Therefore, units 244 and 246 constitute means effective to vary the difference in volumes of the two chambers of each of receptacles 200 and 202 and in that way to vary the proportions of the first and second fluids admitted to chambers 206 and 212 irrespective of the flow rate of the fluids.

As noted hereabove, this adjustment is possible only in certain circumstances. It will be apparent that for the adjustment to be effective the work load imposed by the adjustment mechanism, i.e., the work required to overcome the resistance of connections 240 and 242 and the work required to move the pistons of the adjusting mechanisms, must be less than that imposed by the second fluid inlet. If the reverse condition prevails, all of the make up liquid will be drawn through inlet 230. As such, the flow resistance at the second fluid inlet must be greater than that at connections 240 and 242. This condition is satisfied when the second fluid inlet is constituted by the membrane of the dialysis cell and can be achieved in other ways, as for example, by arranging that a liquid inlet load be applied to the second liquid inlet.

A further embodiment of the invention is illustrated in FIG. 4 and that embodiment operates substantially similarly to the embodiment of FIG. 1 except that a receptacle 300 replaces the piston/cylinder units of the embodiment of FIG. 1 that receptacle being divided into chambers 302 and 304 by a flexible diaphragm element 306. Projecting from one side of the diaphragm to the exterior of the receptacle is a rod element 308 which is effective to cause the volume of the first fluid admitted to chamber 304 to be lesser than that required to fill chamber 302 by an amount directly related to the cross sectional area of the rod. In this way during reciprocation of the diaphragm a second fluid will be drawn into chamber 302 through inlet 310 in an amount equal to the difference in the volumes of the chambers 302 and 304.

As in the embodiment of FIG. 3, it is possible and in some instances may be desirable to provide a piston/cylinder unit 312 comprising a cylinder 314 with a plunger 316 and an adjustable screw threaded stop 318 so that by adjustment of the position of the stop 318 the quantity of the first fluid admitted to the chamber 304 can be varied in this way to vary the proportions of the mixture of the two fluids admitted to chamber 302 since, of course, the effective volume of chamber 302 remains constant.

The embodiment of FIG. 5 shows a somewhat different structure in which a single acting piston and cylinder unit 400 is provided as well as a double acting piston/cylinder unit 402. The piston 404 of piston/cylinder unit 400 has its rod 406 connected, through connecting rod 408 to a driven crank 410. Similarly, piston 412 of piston/cylinder unit 402 has its rod 414 connected by connecting rod 416 to the driven crank 410. The throws of the two connecting rods are similar and the diameter of the cylinder of unit 400 is made to be lesser than that of unit 402 so that during a complete revolution of the crank, piston 404 of unit 400 sweeps a similar volume in chamber 418 to that swept by piston 412 in chamber 420. It will be recognized that it is possible to have this end achieved by arranging that the cylinders be of the same diameter and that the piston 404 be provided with an idler piston rod, identical to rod 414, projecting from its right hand face through the opposed end wall of the cylinder of unit 400.

A source of first fluid is connected to line 422 and, through a one-way poppet valve 424 (or any convenient form of valve) to chamber 418 through branch conduit 426. Conduit 422 continues past one-way valve 428 to a branch 430 leading to chamber 420 of the cylinder of unit 402 and through branch 432 to port 434 of a three port valve 436. From port 438 of valve 436, line 440 leads to chamber 442 of unit 402. From port 444 of valve 436, line 446 leads to waste.

A source of second liquid is connected to conduit 448 which leads to conduit 432.

The operation of the device of FIG. 5 is as follows:

As the crank turns to cause piston 404 to move left to right, liquid contained in chamber 418 will be caused to move past valve 428 and through branch conduit 430 to chamber 420 which will be expanding at the same rate that chamber 418 contracts. Since the volume displaced from chamber 418 is equal to that called for by chamber 420, there will be no flow of second liquid in line 448. As the piston 412 moves right to left the liquid in chamber 442 will pass through line 440 and through ports 438 and 444 of valve 436 to waste at 446. Upon the completion of left to right movement of piston 404 valve 436 will be shifted to its chain line position and as the piston 404 moves right to left, first liquid will enter through conduit 422 to fill chamber 418 past valve 424. Liquid will be prevented from entering chamber 418 past valve 428 and as the chamber 420 of unit 402 begins to contract, the liquid contained in that chamber will be pushed through conduits 430 and 432 through the ports 434 and 438 of valve 436 to chamber 442. Since chamber 442 is of greater volume than chamber 420 and since valve 428 is arranged to have a greater resistance to the passage of liquid than is conduit 448 connecting the source of second liquid to conduit 432, second liquid will be drawn into chamber 442 to make up for the difference in volume.

As the crank 410 continues to rotate, the cycle will be repeated. It will be recognized that as with the embodiments of FIGS. 1 through 4 the source of first liquid may be a dialysate solution and the second liquid may be blood wastes drawn across a dialysis cell.

FIG. 6 shows, schematically, apparatus similar to that of FIG. 1 with means for adjusting the proportion of first to second liquids.

In that embodiment, the piston/cylinder unit is indicated generally at 500 and comprises a cylinder 502 divided into chambers 504 and 506 by a piston 508 having a piston rod 510 which is urged left to right as viewed in the drawings by spring 512.

Conduit 514 extends from chamber 504 to three port valve 516 by means of which the chamber is connected, through conduit 518 to a source of first liquid or by conduit 520 to dialysis cell 522.

Chamber 506 is connected by conduit 524, through a three port valve 526, either to the cell 522 by conduit 528 or by conduit 530 to waste. It is to be noted that the conduit 530 includes a centrifugal pump 532 which, together with the spring 512, provides the motive force for piston 508.

Slidably received in the left hand end wall of cylinder 502 is idler rod 536 which has at its end remote from piston 508 an abutment 538 which cooperates with an adjustable stop 540. Idler rod 536 is biased left to right by means of spring 542. The apparatus of FIG. 6 operates substantially similarly to that of FIG. 1. Where, as shown the device is used in a dialysis system, dialysate solution is admitted to chamber 504 of cylinder 502 along lines 518 and 514 as the piston is moved right to left under the influence of pump 532 which is effective to draw the mixture of dialysate solution and blood wastes from chamber 506. Upon the completion of right to left movement of the piston, valves 516 and 526 are switched, the action of the pump 532 is stopped and under the influence of spring 512, the piston begins its left to right movement pushing dialysate solution along lines 514, 520 and 528 through the cell 522 and to chamber 506. Cycling continues as described with reference to FIG. 1.

To adjust the difference in volumes swept in chambers 504 and 506, idler piston rod 536 is provided. It will be appreciated that during left to right movement of piston 508, rod 536, under the influence of spring 542, will move left to right with the piston until such time as abutment 538 strikes against adjustable stop 540. At that time, the rod 536 will be stopped and piston 508 will continue its left to right movement. As the piston reverses, it will move right to left until such time as it strikes against the adjacent end of rod 536, thereafter rod 536 will move together with the piston 508. It will be appreciated that the rod 536 most desirably has the same diameter as rod 510 so that when the stop 540 is adjusted such that idler rod 536 will follow in abutment with piston 508 to the end of the pistons left to right movement, the volume differential between chambers 504 and 506 will be reduced to zero. As such, when the apparatus is applied to a dialysis procedure there will effectively be no pressure differential across the cell and waste will migrate across the cell under the influence of osmotic pressure. To remove this excess volume over that required to fill chamber 506 a simple outlet may be provided, for example in line 528, delivering to a graduated vessel the contents of that vessel being representative of the volumetric quantity of blood wastes migrating across the membrane of the cell during the volumetric equality portion of each cycle.

Figure 7:
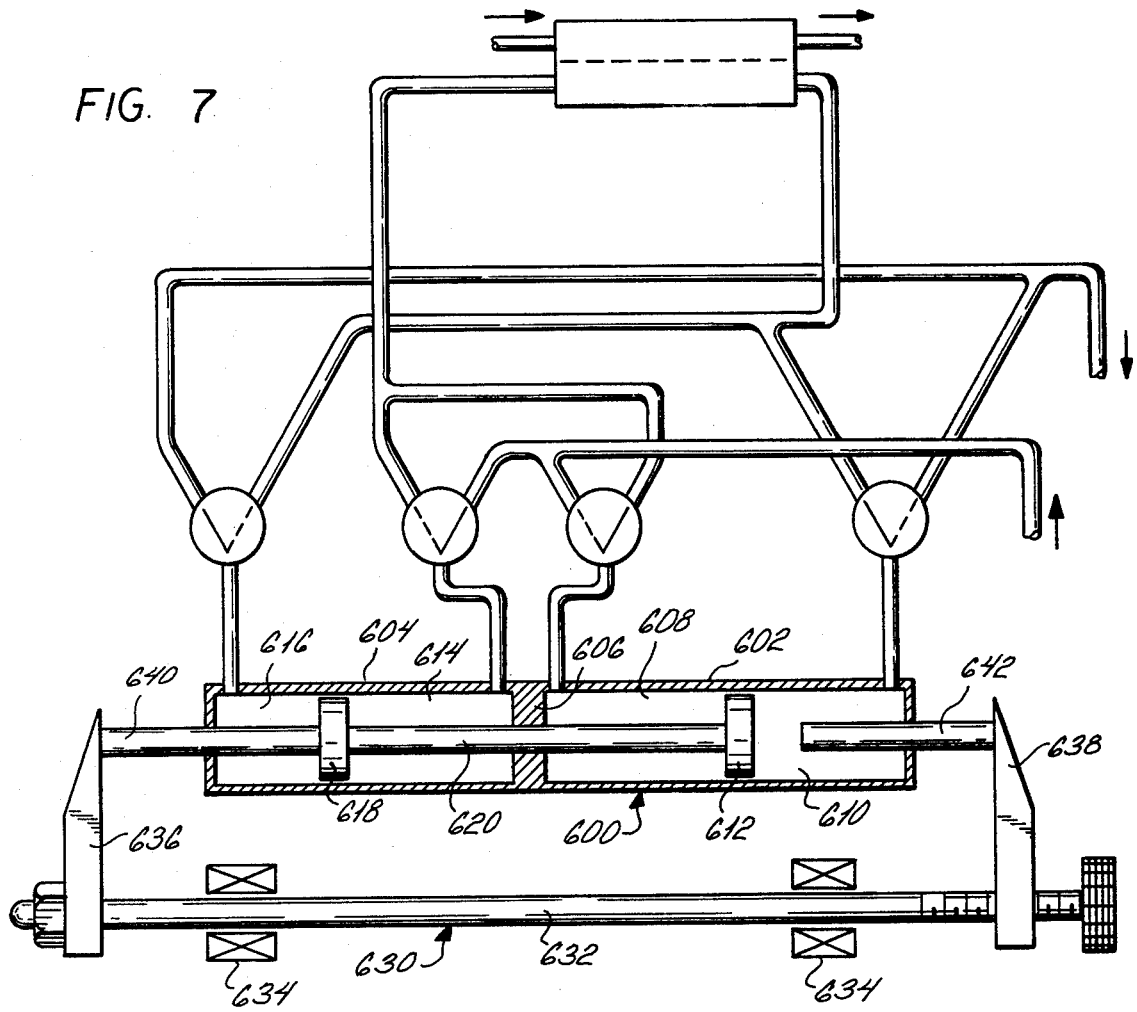
FIG. 7 shows a double acting form of the invention with means for adjusting the proportions of fluids.

The embodiment of the invention of FIG. 7 is in many respects similar to that of FIG. 2, except that three port valves are utilized rather than four port valves. The fluid movement is similar to that in the system of FIG. 2 and for this reason it is not described in detail herein.

The piston/cylinder unit 600 has two cylinders 602 and 604 separated by a common end wall 606. The cylinder 602 is divided into chambers 608 and 610 by a piston 612 and similarly cylinder 604 is divided into chambers 614 and 616 by piston 618, pistons 610 and 618 being interconnected by a constant cross section rod 620 sliding in common end wall 606. Externally of the piston/cylinder unit 600 is a yoke generally indicated at 630, that yoke comprising a slide bar 632 mounted for sliding movement in appropriate bearings 634 for movement parallel to the cylinder axis. Disposed at opposite ends of bar 632 are uprights 636 and 638, respectively, one of those uprights being axially fixed on bar 632 and the other being adjustable therealong so that the spacing between the uprights is selectively variable.

Disposed upon upright 636 is an idler rod 640 and a similar rod 642 is disposed on upright 638 both of those rods being of the same diameter as rod 620. Rods 640 and 642 are slidably received in adjacent end walls of the piston/cylinder unit 600. It will be seen that the distal ends of idler rods 640 and 642 will contact pistons 618 and 610, respectively, as the piston reciprocates in the piston/cylinder unit. It will be appreciated that when the uprights 636 and 638 are adjusted so that the distal ends of rods 640 and 642 contact the pistons simultaneously and when the rods 640 and 642 are of the same diameter as rod 620, the volume differential between chambers 608 and 610 and 614 and 616 will be reduced to zero and that when the spacing is adjusted so that the pistons do not contact the rods 640 and 642 at all, or contact them only at the ends of the stroke, that the volume differential between the chambers will be at the design maximum.

With the embodiments of FIGS. 6 and 7, it will be appreciated that complete adjustability of the volumetric differential between design maximum and zero differential is available.

The embodiment of the invention illustrated in FIG. 8 is one in which the quantity of blood wastes drawn from the membrane of a dialysis cell during each cycle of the piston/cylinder unit can be controlled as desired.

The apparatus of the embodiment of FIG. 8 comprises a piston/cylinder unit 700 having two cylinders 702 and 704 separated by a common end wall 706. Cylinder 702 is divided into chambers 708 and 710 by a piston 712 and cylinder 704 is divided into chambers 714 and 716 by a piston 718. The pistons are interconnected by a constant cross section rod 720 sealingly guided for sliding movement in common end wall 706.

A source of dialysis solution is connected to inlet line 722 leading to port 724 of three port valve 726. From valve 726 by conduits 728 and 730, dialysis solution is led alternately to chambers 710 and 716 of cylinders 702 and 704, respectively. From chambers 710 and 716 of the cylinders, through valve 732, dialysis solution is led to dialysate side 734 of cell 736 and through conduit 738 and valve 740, to chambers 708 and 714 of cylinder 702 and 704, respectively. From chambers 708 and 714 via conduits 740 and 742, respectively, a mixture of dialysis solution, blood wastes and, as described hereinafter, water are passed to waste through valve 744. The operation of the device as thus far described is substantially similar to the basic operation of the devices of FIGS. 1 through 7 and for this reason is not described in detail herein. It is sufficient to say that since the volume of dialysis solution admitted to chambers 710 and 716 is insufficient to fill the chambers 708 and 714 respectively, that the difference in volume must be made up by blood wastes and, as described hereinafter, by liquid from a further source. The liquid from the further source and the blood waste constituting the second liquid discussed supra.

Connected to conduit 738 between the exit of that conduit from the dialysate side of cell 736 and valve 740 is a branch conduit 746 which, through solenoid valve 748 and one-way valve 750, communicates with a source 752 of water.

It is to be recognized that there is a substantial resistance to transmembrane flow of blood wastes from the blood side of cell 736 to the dialysate side of that cell. That resistance to flow is greater than that presented by valves 748 and 750 and conduit 746 when valve 748 is opened. Thus, by controlling the period over which valve 748 is opened, one can control the quantity of blood wastes migrating across the membrane of the cell. When the valve 748 is maintained constantly closed, the flow of blood wastes will equal, in any given cycle of the piston/cylinder unit, the differences between the volumes of chambers 708 and 710 and chamber 716 and 714. Similarly, when valve 748 is maintained constantly open, then there will be no passage of blood wastes across the membrane other than by osmotic migration. Thus it will be appreciated that the volumetric differential may be adjusted between design maximum and zero.

By arranging that the vessel 752 constituting the source of liquid be graduated, knowing the total volumetric differential during a hemodialysis procedure, by computing the number of cycles of the piston/cylinders, one can determine the total of blood waste withdrawal from a patient.

Most desirably, the vessel 752 contains water since necessarily this is very much less expensive than other available liquids and since, of course, the liquid from vessel 752 does not play a direct role in the dialysis procedure, i.e. does not actually enter the cell 736.

A further embodiment of the invention valuable for relatively crude dosing and mixing applications is illustrated in FIG. 9. The embodiment of the invention in that figure comprises a piston/cylinder unit 800 having two cylinders 802 and 804 separated by a common end wall 806. Piston 808 divides cylinder 802 into chambers 810 and 812 and similarly piston 814 divides cylinder 804 into chambers 816 and 818. A source of a first fluid A is connected alternately to chambers 812 and 818 through three port valve 820. Chambers 812 and 818 are connected through valve 822 conduit 824 and valve 826 to chambers 810 and 816, respectively. Chambers 810 and 816 are then connected alternately to outlet conduit 828 through three port valve 830.

A connection 832 from a source of second liquid is made into conduit 824 and since the volumes of chambers 812 and 818 are lesser than those of chambers 810 and 816 as the piston cycles the difference in volumes will be made up by second liquid drawn through conduit 832.

The system as described to this point operates on much the same basic principle as the previously described embodiments. This particular system differs from those previously described embodiments inasmuch as there is provided a by-pass 834 between outlet conduit 828 and conduit 824, that by-pass having a solenoid controlled valve 836. The valve 836 is one which will allow the passage of liquid only from conduit 828 to conduit 824 and not in the reverse direction.

Assuming that the valve 836 is closed, the system of FIG. 9 will operate as follows. With the valves in the position shown in full line, first liquid A will be admitted to chamber 818 and the pistons will move left to right, piston 814 causing liquid contained in chamber 816 to pass through valve 830 to outlet conduit 828. In the meantime, liquid previously admitted to chamber 812 will pass through valve 822 and conduit 824 and valve 826 to chamber 810. Upon completion of left to right movement, the valves will move under an appropriate control, such as any of those described above with reference to others of the figures of the drawings, to the position shown in chain line. At this time, first liquid A will be admitted to chamber 812 and the pistons will commence their right to left movement. Piston 808 will cause liquid in chamber 810, a combination of liquids A and B, to move through valve 830 to outlet conduit 828 while the liquid A admitted to chamber 818 during left to right piston movement will be passed through conduit 824 and valve 826 to chamber 816 and, of course, since chamber 816 is of greater volume than chamber 818 liquid from conduit 832 will be drawn into chamber 816 to make up for the difference in volumes. So long as valve 836 remains closed this cycle will continue indefinitely.

The provision of by-pass 834, valve 836 and an appropriate element to render the resistance to admission of fluid through conduit 832 greater than that through the by-pass 834 of valve 836 such as, for example, a throttling orifice, allows the quantity of fluid admitted through conduit 832 to be varied from zero to design maximum. By opening valve 836 and maintaining that valve constantly open the liquid demanded by the larger volume chambers 810 and 816 to make up for the differences in volumes between those chambers and chambers 812 and 818 will be by-passed through conduit 834 and no second liquid will be admitted through conduit 832. It will be appreciated that by controlling the period over which valve 836 is opened as the piston cycles one can obtin any desired proportion of second liquid B to recycled liquid passing through by-pass 834. In other words, one can obtain mixtures of liquids A and B at outlet 828 in proportions between wholly liquie A and a mixture of liquid A and design maximum of liquid B. It will be recognized that in this instance, the second liquid is constituted in fact by fluid B and the recycled mixture of liquids A and B moved along by-pass 834 and through valve 836.

Figure 10:
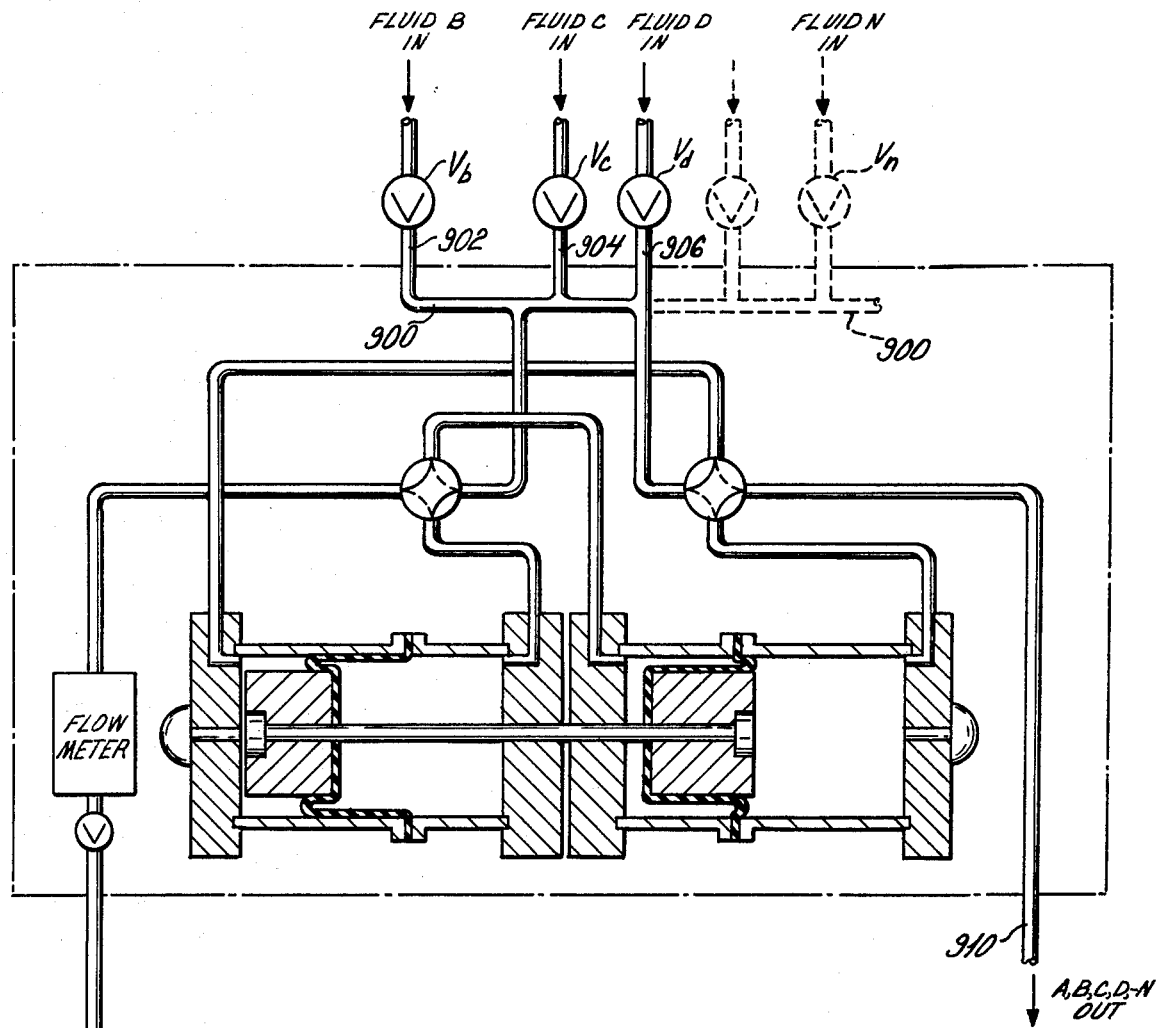
FIG. 10 shows an embodiment of the invention in many respects similar to that illustrated in FIG. 2, but one adapted to handle a second liquid of plural components.

A further variation of the present invention is illustrated in FIG. 10. The embodiment of the invention in FIG. 10 is for the most part similar to that embodiment illustrated in FIG. 2. For this reason only the differences between the embodiment of FIG. 10 and that of FIG. 2 are described. It is to be noted that the second liquid inlet is consituted by a manifold conduit 900 with which a plurality of branch conduits 902, 904, 906— communicate, each one of those branch conduits containing a valve $V_b$, $V_c$, $V_d$—. It will be recognized that by appropriately controlling the valves within the branch conduits one can obtain a desired mixture of the several fluids to be discharged at outlet 910. The valves would be operable to be opened alone for a prescribed portion of each half cycle of the piston/cylinder unit. It will be recognized that in this embodiment that accurate proportioning can be achieved by opening only one valve at any given time, in this way to eliminate error originating from differences in resistance between the materials to be added through the various branch conduits.

Still a further embodiment of the invention is illustrated in FIG. 11 which comprises a system substantially similar to that described with respect to FIG. 8, but in which the liquid B inlet is constituted by a simple conduit as distinct from the membrane of a dialysis cell and in which instead of employing a solenoid operated valve to control the admission of the second component, liquid C, of the second liquid one utilizes a metering pump 1002. By appropriately controlling the metering pump to inject or extract from the system a desired quantity of liquid C one can control the make-up of the mixture of liquids A, B, and C issuing from outlet 1004.

This invention has been described with particular reference to its utilization in the mixing of fluids and while it is envisaged that in each application of the invention fluids will be mixed, it is not a requirement that the mixed fluids be utilized. As for example, where the apparatus is used in a dialysis system, the second fluid would be constituted by blood wastes and the second fluid inlet would comprise the semipermeable membrane of the dialysis cell. Obviously, in other situations, as for example in the preparation of solutions such as dialysate solutions, the first fluid would be water, appropriately heated, filtered, pressurized and otherwise pretreated, while the second fluid would be a dialysate concentrate material.

Besides the applications in the field of dialysis, it is to be appreciated that the apparatus may find use in a system, for example, for mixing fluids containing vitamins with, for example, milk, where the milk would constitute the first fluid and the vitamins the second fluid.

It is also to be appreciated that by the careful selection of the difference in volume swept by the piston to either end of that piston, different proportions of fluids in the resultant mixture can be obtained and if necessary the pistons may be provided with what would in effect be merely idler piston rods which project from those ends of the pistons which, in the embodiments of the invention illustrated, are without a piston rod. This would be desirable, for example, where the amount of the second fluid required in a mixture, relative to that of the first fluid, is so small that the volume to be occupied by a single piston rod would require that the piston rod be less sturdy than necessary. In that instance, the rod in the chamber of lesser volume would be of larger diameter than the rod in the chamber of greater volume.

What is claimed is:

1. A method of proportioning and mixing liquids which comprises delivering a predetermined volume of first liquid to a first chamber to fill that chamber, making a connection from said first chamber to a second and larger chamber and passing said volume of first liquid from said first chamber to said second chamber through said connection while preventing the admission of further first liquid to said first chamber and connecting a supply of liquid to be mixed with said first liquid to said connection between said first and second chambers to cause said liquid to be mixed to be admitted to said connection and to said second chamber in an amount equal to the difference in volumes of said chambers.

2. Method as claimed in claim 1 wherein said first and second chambers are defined within a common receptacle and are separated by movable partition means and wherein said movable partition means is reciprocated within said receptacle to cause said first chamber to expand as said predetermined volume of first liquid is delivered thereto and to cause said second chamber to expand as said volume of first liquid is passed from said first chamber to said second chamber.

3. Method as claimed in claim 2 which comprises counting the number of reciprocations of said partition means.

4. Method as claimed in claim 2 which consists in adjusting the difference in volume between said chambers.

5. Method as claimed in claim 1 wherein said supply of liquid to be mixed includes at least two separate liquid sources.

6. Method as claimed in claim 5 which comprises controlling the admission of liquid through at least one of said separate sources.

7. Method as claimed in claim 5 wherein each said sources includes conduit means leading to said connection, one of said conduit means presenting a greater resistance to liquid flow therethrough than the remaining ones of said conduit means, said remaining ones of said conduit means including flow control means.

8. Method as claimed in claim 7 wherein said conduit means presenting a greater resistance to liquid flow comprises a membrane of a hemodialysis cell.

9. Method as claimed in claim 8 wherein said flow control means comprises valves.

10. Method as claimed in claim 5 wherein mixed liquids are conducted from said second chamber through outlet conduit means, said conduit means constituting one of said separate sources and including a by-pass to said connection, said by-pass including valve means and wherein said valve means is controlled to vary the components of liquids to be mixed from said sources.

11. Method as claimed in claim 5 wherein one of said sources includes metering pump means and wherein said metering pump means is controlled to adjust that quantity of liquid to be mixed admitted through said one source.

12. Method as claimed in claim 5 comprising two separate sources each source including conduit means communicating with said connection one of said conduit means comprising the membrane of a hemodialysis cell and the other comprising a solenoid controlled valve and means for measuring liquid passing said solenoid valve and wherein liquid passing said solenoid valve is measured.

13. Method as claimed in claim 5 wherein different liquids are passed from said separate sources to said connection the quantity of at least one of said different liquids being controlled.

14. Liquid proportioning and mixing apparatus comprising a liquid filled system including a first receiving chamber receiving a predetermined volume of a primary liquid, a second receiving chamber, means connecting said chambers, means transporting liquid from said first chamber to said second chamber through said connecting means, at least two liquid inlet means for secondary liquid communicating with said connecting means and means rendering the volume of said second chamber greater than said predetermined volume of primary liquid, whereby liquid is delivered through at least one of said inlet means to said connecting means to fill, with said primary liquid, said second chamber.

15. Apparatus as claimed in claim 14 comprising flow control means associated with at least one of said liquid inlet means.

16. Liquid proportioning and mixing apparatus comprising a source of a primary liquid and filled system including a first receiving chamber receiving a predetermined volume of a primary liquid from said source, a second receiving chamber, means connecting said chambers, means transporting liquid from said first chamber to said second chamber through said connecting means, a source of secondary liquid, connecting means extending between said secondary source and said means connecting said chambers and means rendering the volume of said second chamber greater than said predetermined volume of primary liquid, whereby secondary liquid is delivered through said connecting means and said means connecting said chambers, to fill, with said primary liquid, said second chamber, said source of secondary liquid comprising at least two supplies of different liquids and means controlling the quantity of liquid admitted from one of said supplies.

17. An apparatus as claimed in claim 16 wherein one of said supplies of liquids is constituted by the blood side of a hemodialysis cell and the other of said supplies is provided with means controlling the admission of liquid to said connecting means.

18. An apparatus as claimed in claim 17 wherein said means controlling the admission of liquid comprises valve means.

19. An apparatus as claimed in claim 16 wherein said means controlling the admission of liquid from one of said supplies comprises metering pump means in said supply.

* * * * *